United States Patent [19]

Chen

[11] Patent Number: 4,761,710

[45] Date of Patent: Aug. 2, 1988

[54] POLYIMIDE CAPACITIVE HUMIDITY SENSING ELEMENT

[75] Inventor: Stephen G. L. Chen, Tainan Hsien, Taiwan

[73] Assignee: Industrial Technology Research Institute, Hsin-Chu, Taiwan

[21] Appl. No.: 65,830

[22] Filed: Jun. 23, 1987

[51] Int. Cl.[4] .................... H01G 7/00; G01N 27/12
[52] U.S. Cl. ..................................................... 361/286
[58] Field of Search ...................... 361/286; 73/336.5

[56] References Cited

U.S. PATENT DOCUMENTS

| | | | |
|---|---|---|---|
| 3,983,527 | 9/1976 | Ohsato et al. | 73/336.5 X |
| 4,164,868 | 8/1979 | Suntola | 73/336.5 |
| 4,305,112 | 12/1981 | Heywang et al. | 361/286 |
| 4,345,301 | 8/1982 | Nelson | 73/336.5 X |
| 4,696,796 | 9/1987 | Oka et al. | 73/336.5 X |

FOREIGN PATENT DOCUMENTS 139097  10/1979  Japan .................... 73/336.5

Primary Examiner—Donald A. Griffin
Attorney, Agent, or Firm—Ladas & Parry

[57] ABSTRACT

The present invention relates to a humidity sensing element having a polyimide moisture sensing film. It is of a capacitive structure containing, without the use of adhesives, a polyimide film which is either sandwiched between a corrosion resisting metal substrate and a thin moisture permeable gold layer, or vapor deposited on both sides thereof with a moisture permeable thin gold layer.

11 Claims, 3 Drawing Sheets

POLYIMIDE CAPACITIVE HUMIDITY SENSING ELEMENT

DETAILED DESCRIPTION

BACKGROUND OF THE INVENTION

The application of moisture sensing elements in modern living are getting more important. The increasing demand, especially in the areas of air conditioning, environmental control and agricultural equipment has shown distinctive growth.

At present, the materials used for humidity sensing are in three categories: (1) electrolyts, (2) fine ceramics and (3) polymers.

The advantages of fine ceramics are high stability and good thermal resistance, but they tend to have narrow measuring temperature range. Furthermore, the moisture retention due to capillary phenomenon exhibited in ceramics delineates a rather apparent hysteresis.

Polymers show less hystersis, but exhibit inferior thermal resistance. The range of operating temperatures also is quite low, with poor stability.

The principle of humidity sensing in the polymers can be divided into two types; the resistance and capacitance. The capacitance change derived from the change of dielectric constant due to moisture content variation follows the equation shown below:

C: Capacitance
$\epsilon$: Dielectric constant
A: Electrodes surface area
D: Distance between two electrodes Polyimide exhibits excellent heat resisting property and is a hygroscopic insulating material. Its capacitance varies with the dielectric constant due to moisture content variation. Thus, the atmospheric moisture content can be measured.

Because the dielectric constant of polyimide is linearly proportional to its moisture content, consequently, the humidity sensing also exhibits linearity. Furthermore, the excellent thermal resistance of polyimide renders its usefulness recently in the capacitive humidity sensing element which can be found in U.S. Pat. Nos. 4,305,112 and 4,345,301.

For example, U.S. Pat. No. 4,305,112 relates to a capacitive humidity sensing element with a multi-layer structure. It comprises at least a humidity sensing and a moisture permeable, electricity conducting metal layers and these two layers and the substrate are bonded with adhesives. The humidity sensing layer is a soluble polyimide which is derived from imidization. Therefore, the bonding between the layers of polyimide and metal substrate can only be readily achieved by using adhesives. In turn, the promoter used not only interferes with the polyimide hygroscopic property and sensing humidity accuracy, but also increases the complexity of actual manufacturing process as well.

On the other hand, U.S. Pat. No. 4,345,301 relates to a capacitive humidity transducer which comprises two electricity conducting coatings on both sides of polyimide layer as parallel capacitance plates. These two plates are copper coated and both need electrical connectors. Copper electrodes are readily corroded in the presence of moisture. Thus it renders less desirable for long term applications. In addiiton, its construction is more complex than the present invention.

SUMMARY OF THE INVENTION

The object of the present invention is to provide a polyimide capacitive humidity sensing element having better stability, excellent humidity sensing and faster response time by a suitable process without using adhesives.

To achieve this object, a humidity sensing element is coated onto the metal substrate with either a polyimide precursor or a mixture of soluble polyimide and its precursor. After drying, another moisture permeable layer of thin gold electrode is coated thereon which produces a polyimide capacitive humidity sensing element.

In another manufacturing process, both sides of the polyimide film are vapor deposited with moisture permeable thin gold layers as a capacitive humidity sensing element.

BRIEF DESCRIPTION OF THE DRAWINGS

FIG. 2-1 is a front view of the pattern type gold electrode.

DESCRIPTION OF THE INVENTION

In this invention, the polyimide is produced by the reaction between dianhydride and diamine in a polar solvent followed by dehydration under heat. The dianhydrides used include pyromellitic dianhydride and 3,3'-4,4'-benzophenon tetracarboxylic acid dianhydride, whereas the diamines used include p-phenylene diamine, m-phenylene diamine, 4,4'-diamino-diphenyl methane, 4,4'-diamino-diphenyl ether, 3,4'-diamino-diphenyl ether and 4,4'-diamino-diphenyl sulfide, and N-methyl-pyrrolidone is used as the polar solvent.

Figure 1:
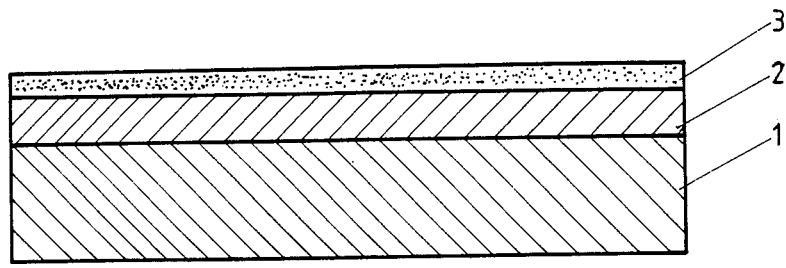
FIG. 1 is a side view of a humidity sensing element of a continuous thin gold electrode type in which 1 refers to substrate 2 to polyimide film and 3 to continuous thin gold electrode.

The process for manufacturing the element shown in FIG. 1 without using adhesives is follows: first, the polyamic acid(polyimide precursor) or mixture of polyamic acid and soluble polyimide (2) which is already imidized is applied to the substrate (1), then the metal substrate along with the dried preliminary coating is tempered with a gradual temperature increase until it reaches approximately 350° C. In this manner, a layer of polyimide film can be manufactured with thickness in the range of 0.1–50 $\mu$m. Then the polyimide film is coated by vacuum vapor deposition with a thin gold layer which functions as a moisture permeable thin gold electrode (3).

Figure 2:
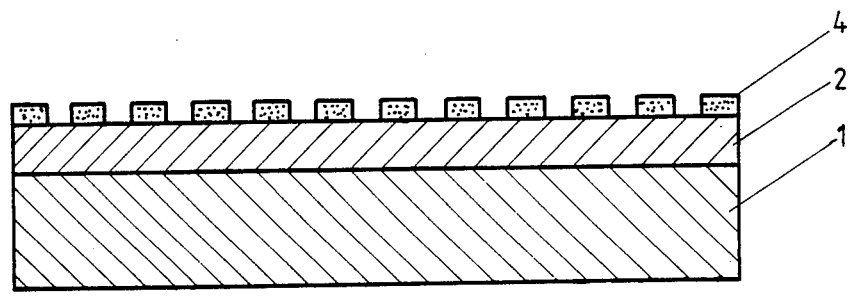
FIG. 2 is a side view of a humidity sensing element of gold electrode of pattern type, in which 1 and 2 refer to the same as in FIG. 1 whereas 4 to gold electrode of pattern type.
Figures 1, 2:

The process for manufacturing the element shown in FIG. 2 is similar to that shown in FIG. 1. The only difference is that the moisture permeable thin gold electrode pattern on the top of the polyimide film is etched microlithographically. FIG. 2-1 exemplifies two etched patterns of the gold electrode, one comprising mutually parallel etched strips and the other comprising a plurality of evenly spaced circular etched areas.

Figure 3:
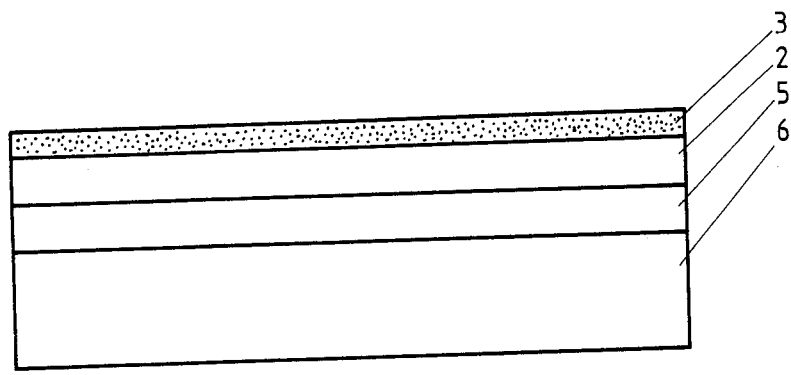
FIG. 3 is a side view of a capacitive humidity sensing element using an insulating substrate coated with a metal layer on the top thereof as a lower electrode, in which 2 and 4 refer to same as in FIG. 1, whereas 5 to corrosion resistant metal layer and 6 to insulating substrate.

The process for manufacturing the element shown in FIG. 3 is first to vapor deposit a corresion resisting metal, such as gold or platinum, onto the insulation substrate (6), bond the metal layer and the substrate closely by sintering, and finally add a coating thereon of polyimide film and thin gold electrode, respectively, as described in FIG. 1.

Figure 4:
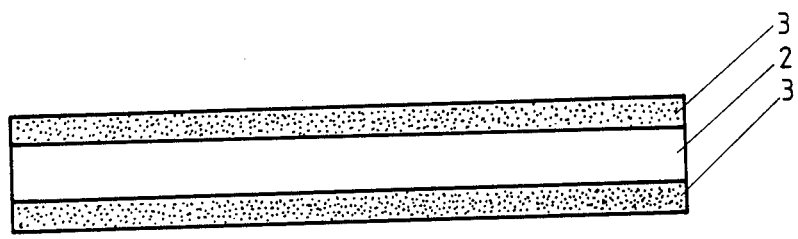
FIG. 4 shows a polyimide film humidity sensing element with gold electrode coated on both sides thereof, in which 2 and 3 refer to same as in FIG. 1.

The process for manufacturing the element shown in FIG. 4 is to vapor deposit a thin gold electrode on both sides of the polyimide film.

DESCRIPTION OF THE PREFERRED EMBODIMENT

Figure 5:
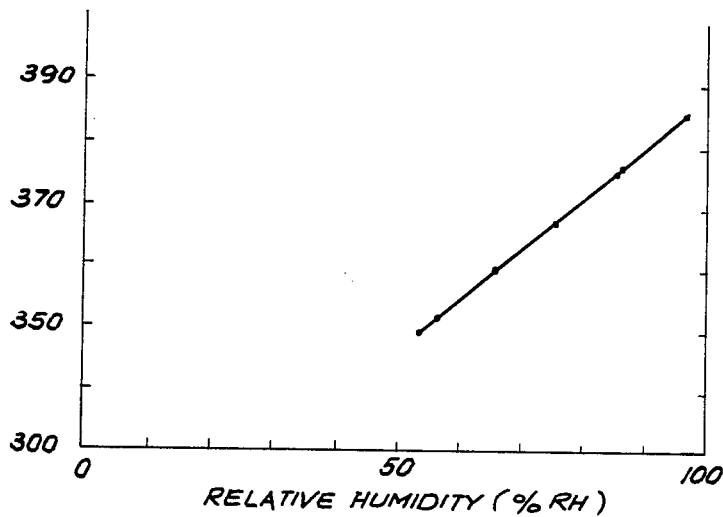
FIG. 5 shows the humidity sensing characteristics of the humidity sensing element shown in FIG. 1.
Figure 6:
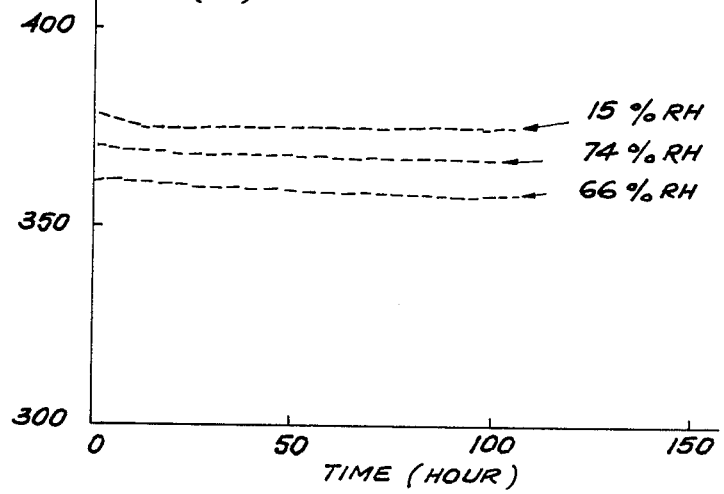
FIG. 6 shows the stability test of said humidity sensing element.

The synthetic polyimide precursor derived from the solution of 3,3'-4,4'-benzophenone tetracarboxylic dianhydride and p-phenylene diamine dissolved in N-methyl-2-pyrrolidone is coated onto a stainless steel substrate. This coated substrate is heated in steps from ambient temperature to approximately 350° C. to form thereon a polyimide film of about 20 μm in thickness, followed by vacuum vapor deposition of gold to obtain the humidity sensing element as shown in FIG. 1. Its humidity sensing characteristics are described in FIG. 5. The method of testing is to record the capacitance change under different relative humidity at a constant temperature (25±0.1° C.) and in a humidity chamber. It can be seen from FIG. 6, that the error is less than 2% relative humidity after 100 hours of testing. It is indicative that this humidity sensing element without using adhesives still shows excellent stability.

The adhesion test results for the bonding properties between the polyimide film and stainless steel substrate obtained from the above manufacturing process is tabulated in Table 1. The testing specification is based upon ASTM D3359-78. It is readily seen that excellent adhesion exhibits between polyimide film and stainless steel substrate.

TABLE 1

| Time | Initial | 1000 hr | 1500 hr |
|------|---------|---------|---------|
| Grade | 5 | 5 | 5 |

Temp.: 25° C. Relative Humidity: 96% RH

I claim:

1. A capacitive humidity sensing element comprising:
   a corrosion resistant metal substrate;
   a humidity sensitive polyimide film coated on the corrosion resistant metal substrate; and
   a moisture permeable thin gold electrode on top of the humidity sensitive polyimide film, the humidity sensitive polyimide film being produced by reacting:
   a dianhydride selected from the group consisting of pyromellitic dianhydride and 3,3'-4,4'-benzophenon tetracarboxylic acid dianhydride, with
   a diamine selected from the group consisting of p-phenylene diamine, m-phenylene diamine, 4,4'-diamino-diphenyl methane, 4,4'-diamino-diphenyl ether, 3,4'-diamino-diphenyl ether and 4,4'-diamino-diphenyl sulfide.

2. A capacitive humidity sensing element according to claim 1, wherein the dianhydride and the diamine are reacted in a polar solvent.

3. A capacitive humidity sensing element according to claim 1, wherein the moisture permeable thin gold electrode is vapor deposited onto the humidity sensitive polyimide film.

4. A capacitive humidity sensing element according to claim 1, wherein the moisture permeable thin gold electrode is formed as a continuous layer.

5. A capacitive humidity sensing element according to claim 1, wherein the moisture permeable thin gold electrode is formed as a patterned layer.

6. A capacitive humidity sensing element according to claim 1, wherein the corrosion resistant metal substrate is made of a metal selected from the group consisting of stainless steel, gold, platinum and nickel.

7. A capacitive humidity sensing element according to claim 6, wherein the corrosion resistant metal substrate is further secured onto an insulating material.

8. A capacitive humidity sensing element according to claim 7, wherein the metal substrate is vapor deposited onto the moisture sensitive polyimide film.

9. A capacitive humidity sensing element according to claim 6, wherein the corrosion resistant metal substrate is made of gold and is moisture permeable.

10. A process for producing a capacitive humidity sensing element comprising the steps of:
   (i) coating a solution of a dianhydride selected from the group consisting of pyromellitic dianhydride and 3,3'-4,4'-benzophenon tetracarboxylic acid dianhydride, and a diamine selected from the group consisting of p-phenylene diamine, m-phenylene diamine, 4,4'-diamino-diphenyl methane, 4,4'-diamino-phenylene diamine, 4,4'-diamino-diphenyl methane, 4,4'-diamino-diphenyl ether, 3,4'-diamino-diphenyl ether and 4,4'-diamino-diphenyl sulfide in a polar solvent onto a corrosion resistant metal substrate;
   (ii) heating the coated substrate in stages to a temperature between 200° and 300 ° C. until a humidity sensitive polyimide film is formed on the substrate; and
   (iii) coating a thin gold layer onto the humidity sensitive polyimide film.

11. A process according to claim 10, wherein the polar solvent is N-methyl-pyrrolidone.

* * * * *